United States Patent [19]

Ochiai et al.

[11] Patent Number: 5,081,866
[45] Date of Patent: Jan. 21, 1992

[54] RESPIRATORY AIR FLOWMETER

[75] Inventors: Koichi Ochiai; Shigeru Aoshima; Shoji Kamiunten, all of Kanagawa, Japan

[73] Assignee: Yamatake-Honeywell Co., Ltd., Tokyo, Japan

[21] Appl. No.: 530,237

[22] Filed: May 30, 1990

[51] Int. Cl.[5] ............................................. G01F 1/68
[52] U.S. Cl. ................................. 73/204.21; 128/724
[58] Field of Search ........... 73/204.16, 204.21, 204.22, 73/204.23, 204.25, 204.26; 128/724, 725

[56] References Cited

U.S. PATENT DOCUMENTS

| | | | |
|---|---|---|---|
| 3,433,069 | 3/1969 | Trageser | 73/204.21 |
| 3,645,133 | 2/1972 | Simeth et al. | 73/204.21 |
| 3,800,592 | 4/1974 | Jones, Jr. | 73/204.16 |
| 4,363,238 | 12/1982 | William | 73/204.21 |
| 4,829,818 | 5/1989 | Bohrer | 73/204.22 |
| 4,972,708 | 11/1990 | Wiegleb et al. | 73/204.22 |

Primary Examiner—Herbert Goldstein
Attorney, Agent, or Firm—Blakely, Sokoloff, Taylor & Zafman

[57] ABSTRACT

A respiratory air flowmeter includes a flow path forming member, a restricting portion, rectifying lattices, and a sensor. The flow path forming member forms a flow path in which respiratory air flows. The restricting portion and the rectifying lattices are arranged in the flow path in order to stabilize a respiratory air flow. The sensor is mounted in a sensor mounting portion of the flow path forming member, and detects a flow rate of respiratory air flowing in the flow path.

9 Claims, 2 Drawing Sheets

RESPIRATORY AIR FLOWMETER

BACKGROUND OF THE INVENTION

The present invention relates to a respiratory air flowmeter used for medical applications.

Various conventional clinical methods of measuring the flow rate of respiratory air of a patient are known, e.g., (1) a method of using a resistance tube, (2) a method of using a hot-wire anemometer, (3) a method of using a variable orifice, and (4) a method of using a body plethysmograph.

In the method of using a resistance tube, a tube having a resistance arranged midway along its tube path is inserted in a patient, and the flow rate of respiratory air of the patient is measured on the basis of a difference between pressures before and after the resistance. The overall tube is heavy and is difficult to be mounted in the patient. In addition, the tube is expensive. The tube must be cleaned every time it is used and requires a cumbersome handling. Moreover, the tube cannot correctly respond as the speed of respiration is increased. In the method of using a hot-wire anemometer, various disadvantages are posed, e.g., requiring a large, expensive apparatus, calibration for every measurement, difficult handling, special care in measurement of a reciprocating flow, and dangerous for a patient when the hot-wire is disconnected. In contrast to this, the method of using a variable orifice is advantageous in that it has a simple structure. However, it has a critical disadvantage, i.e., low precision. In the method of using a body plethysmograph, a patient enters a box having a volume of about 500 l, and the flow rate of respiratory air is measured on the basis of a change in volume or pressure caused by respiration. This requires a large, expensive apparatus. In addition, since temperatures, atmospheric pressures, and the like must be corrected, and the patient must be moved, measurement cannot be easily performed.

SUMMARY OF THE INVENTION

It is, therefore, an object of the present invention to solve the conventional problems described above and provide a small, light respiratory air flowmeter which is easy to handle, causes little suffering to a patient, can be provided at low cost so as to be disposable, and can respond to a change from a forward flow to a reverse flow at high speed.

In order to achieve the above object, according to the present invention, there is provided a respiratory air flowmeter comprising a flow path forming member for forming a flow path in which respiratory air flows, a restricting portion and a rectifying lattice, arranged in the flow path, for stabilizing a respiratory air flow, and a sensor, mounted in a sensor mounting portion of the flow path forming member, for detecting a flow rate of respiratory air flowing in the flow path.

According to the present invention, when respiratory air flows in the flow path of the flow path forming member, the respiratory air is rectified by the rectifying lattice and the restricting portion and becomes a stable flow. When the stable flow is brought into contact with the sensor, the sensor outputs a stable signal upon detection of the flow. When the detection signal is processed by a processor, the flow rate of the respiratory air is measured.

DETAILED DESCRIPTION OF THE PREFERRED EMBODIMENT

The present invention will be described in detail below with reference to an embodiment illustrated in the accompanying drawings.

Figure 1:
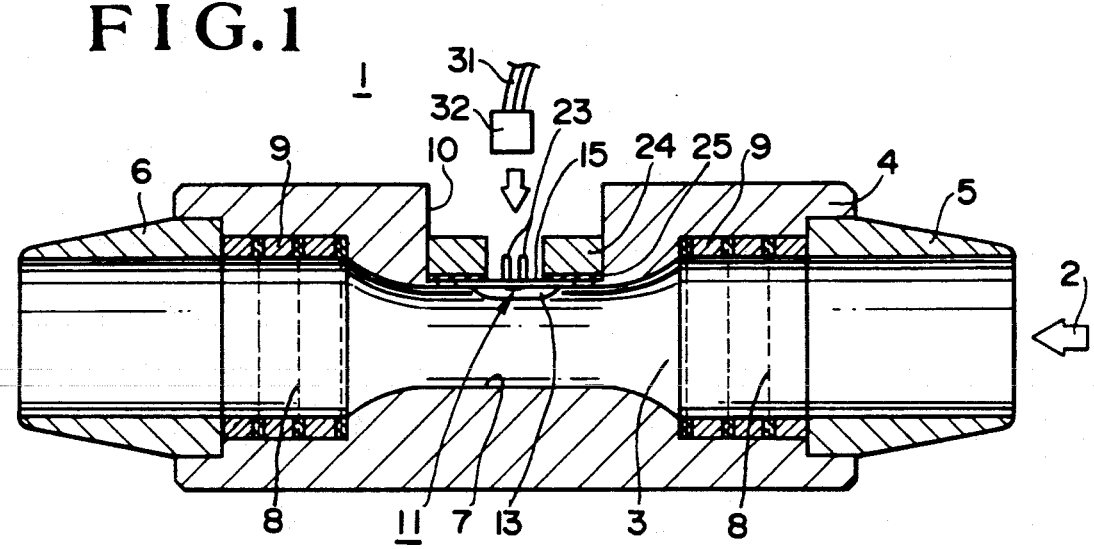
FIG. 1 is a sectional view showing a respiratory air flowmeter according to an embodiment of the present invention.
Figure 2:
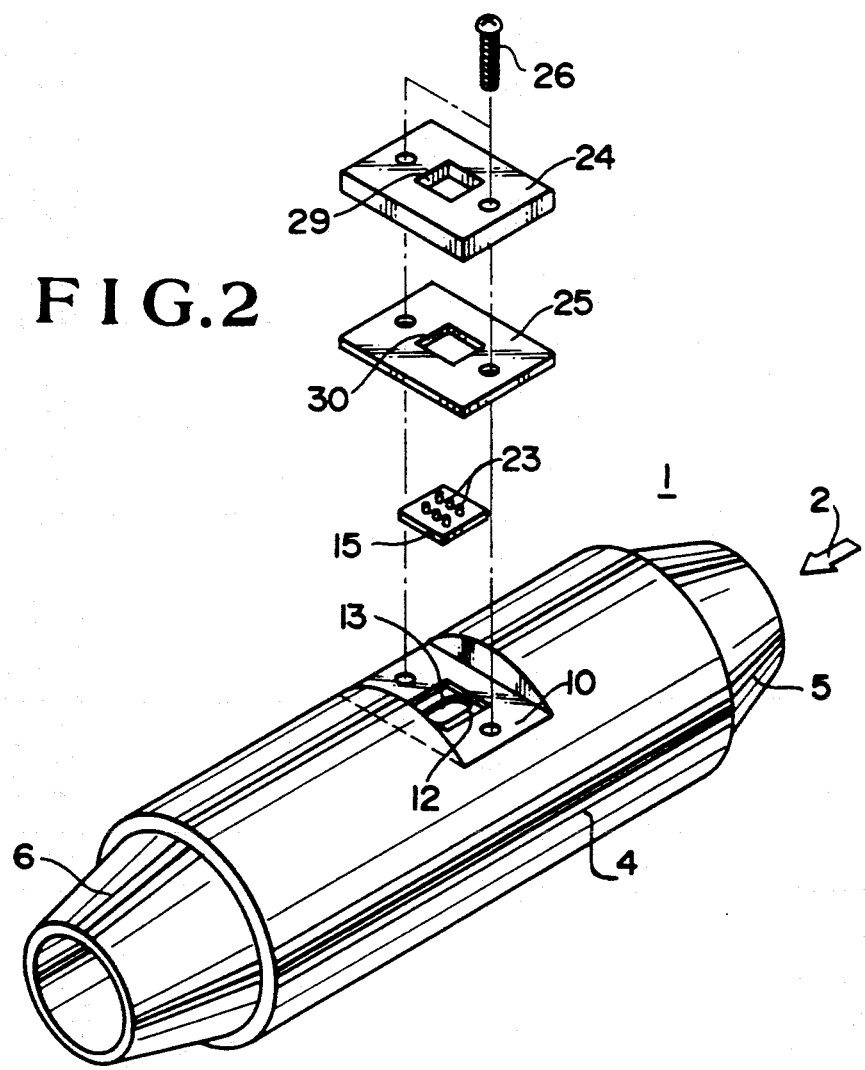
FIG. 2 is an exploded perspective view of the respiratory air flowmeter.
Figure 3:
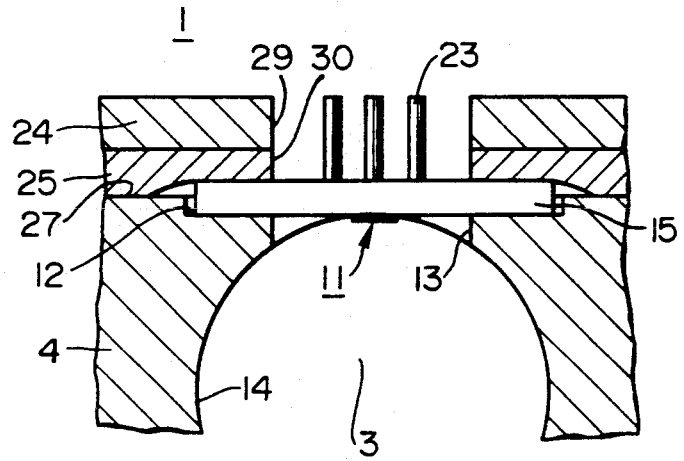
FIG. 3 is a sectional view showing a main part of the respiratory air flowmeter.
Figure 4:
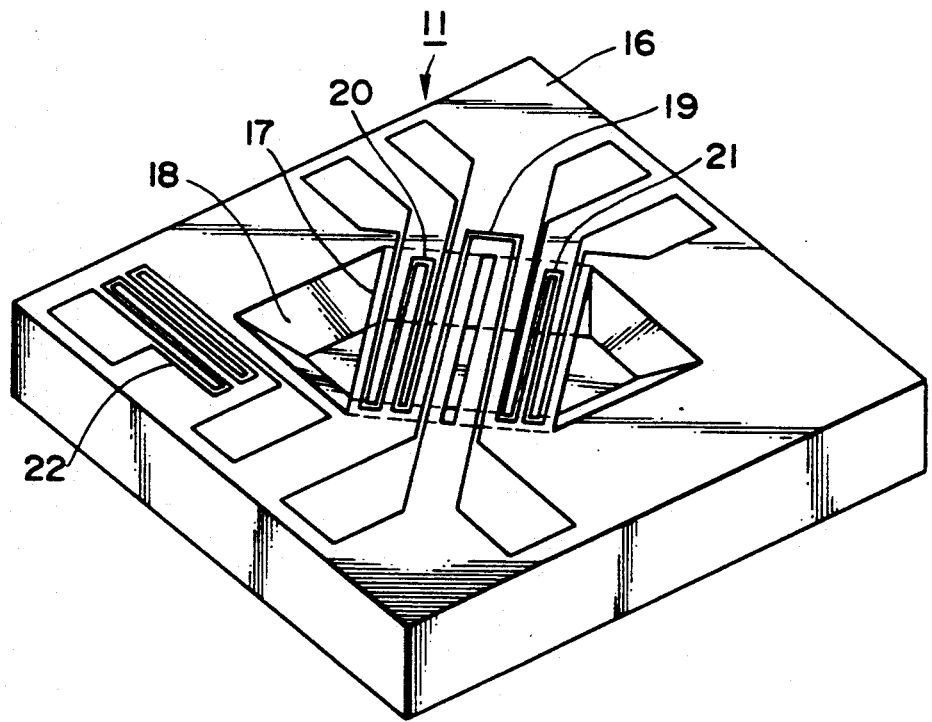
FIG. 4 is a perspective view of a sensor.

FIGS. 1 to 3 show a respiratory air flowmeter according to an embodiment of the present invention. FIG. 4 shows a sensor. Referring to FIGS. 1 to 3, a respiratory air flowmeter denoted by reference symbol 1 as a whole includes a cylindrical flow path forming member 4 for forming a flow path 3 in which respiratory air 2 is supplied. Couplings 5 and 6 having tapered outer and inner surfaces are fitted/fixed in the respective openings of the flow path forming member 4. A middle portion of the member 4 is reduced in inner diameter to form a restricting portion 7 for stabilizing the flow of the respiratory air 2. In addition, a plurality of rectifying lattices 8 for stabilizing the flow of the respiratory air 2 are respectively arranged between the restricting portion 7 and the couplings 5 and 6 through rectifying lattice stop rings 9. A recess as a sensor mounting portion 10 in which a sensor 11 is mounted is formed in a middle portion of the outer surface of the flow path forming member 4 in the longitudinal direction. A recess as a sensor board seat surface 12 (FIG. 3) is formed in a central portion of the bottom of the sensor mounting portion 10 together with a sensor window 13 for causing the flow path 3 to communicate with the sensor mounting portion 10. The board seat surface 12 is formed to be in contact with an inner wall 14 of the flow path 3.

The sensor 11 constitutes a microsensor, and includes a silicon substrate 16 having a predetermined thickness and size (e.g., 1.7 mm sq and 0.25 mm thick), as shown in FIG. 4. A recess portion 18 having a silicon nitride bridge 17 is formed in a central portion of the upper surface of the silicon substrate 16. A heater 19 and upstream and downstream temperature sensors 20 and 21 are formed on the bridge 17. These sensors 20 and 21 are formed on both the sides of the heater 19. An ambient temperature sensor 22 for measuring an ambient temperature is formed on a portion of the surface of the silicon substrate 16 which does not constitute the bridge 17. With this arrangement, the heater 19 is controlled to have a temperature higher than an ambient temperature by a predetermined degree.

The sensor 11 having such an arrangement is arranged on a central portion of one surface of a sensor board 15 (FIG. 3) made of a ceramic material or the like and having a size of, e.g., 11×12×0.635 mm. A plurality of pins 23 as connectors extend from the other surface of the sensor board 15 opposite the sensor 11 side. These pins 23 are electrically connected to the sensor 11 via through holes (not shown) formed in the sensor board 15. The sensor board 15 is arranged on the board seat surface 12 with the sensor 11 facing the flow path 3 through the sensor window 13, thus tightly sealing the sensor window 13. In addition, a lid 24 is arranged in the sensor mounting portion 10 through a gasket 25 in order to urge/fix the sensor board 15 and seal the sensor window 13. These members 24 and 25 are urged/fixed to the bottom of the sensor mounting portion 10, i.e., a gasket seat surface 27 (FIG. 3) with a plurality of set screws 26 (FIG. 2). The distance from the gasket seat surface 27 to the board seat surface 12 is smaller than the thickness of the sensor board 15. For this reason, the sensor board 15 slightly protrudes upward from the gasket seat surface 27. This allows sealing of the sensor board 15. The lid 24 and the gasket 25 respectively have holes 29 and 30 in their central portions. The holes 29 and 30 are large enough to allow the pins 23 to be inserted. A connector 32 attached to one end of a cord 31 (FIG. 1) is connected to the pins 23. The other end of the cord 31 is connected to a processor (not shown) for processing a signal from the sensor 11.

In the respiratory air flowmeter 1 having such an arrangement, when the respiratory air 2 is supplied into the flow path 3 through the coupling 5, the air is rectified by the rectifying lattices 8. The air is further rectified by the restricting portion 7 to be formed into a stable flow, and the air is brought into contact with the sensor 11. When the respiratory air 2 is brought into contact with the sensor 11, temperature distributions on both the sides of the heater 19 are offset from each other. When this offset is detected by the upstream and downstream temperature sensors 20 and 21 on both the sides of the heater 19, it is detected that the respiratory air 2 is flowing. The detection signals from these sensor 20 and 21 are supplied to the processor through the cord 31 and are electrically processed, thereby measuring the flow rate of the respiratory air 2.

In this case, since the bridge 17 of the sensor 11 is not in contact with the silicon substrate 16, the heat capacity of the sensor 11 is small. This allows the sensor 11 to have a high response speed. In addition, since the two temperature sensors 20 and 21 are used, forward and reverse flows of air can be discriminated by determining which sensor detects a higher temperature. In general, an air flow formed in expiration is defined to be a forward flow, and a temperature detected by the upstream temperature sensor in expiration is lower than that detected by the downstream temperature sensor, and vice versa in inspiration.

In the above-described embodiment, the sensor window 13 is air-tightly sealed by using the gasket 25, the lid 24, and the set screws 26. However, if the pressure of respiratory air is low, the sensor window 13 can be satisfactorily sealed by fixing the sensor board 15 to the board seat surface 12 using only an adhesive tape having the same shape as that of the gasket 25. In this case, since the lid 24 and the set screws 26 are not required, the respiratory air flowmeter can be simplified and reduced in diameter.

If the demand for stable measurement is relatively low, the number of rectifying lattices 8 to be arranged in the flow path 3 can be decreased. This enables a reduction in length of the flow path 3.

As has been described above, according to the respiratory air flowmeter of the present invention, since the rectifying lattices and the restricting portion are arranged in the flow path, respiratory air flowing in the flow path can be guided to the sensor while it is stabilized. This allows high-precision measurement of the flow rate of respiratory air. In addition, since the restricting portion is formed and only the sensor and the rectifying lattices are arranged in the flow path, the respiratory air flowmeter can be greatly simplified in structure and reduced in size and weight. Therefore, even if the flowmeter is attached to the mouth of a patient, he/she suffers little torment. In addition, since there is no possibility that broken internal components enter the body of the patient, the respiratory air flowmeter can be safely used not only as a medical flowmeter but also as a general flowmeter. If a microsensor is used as the sensor, a change from a forward flow to a reverse flow can be detected at high speed. Moreover, since the respiratory air flowmeter of the present invention can be provided at a low cost, it may be used as a disposable flowmeter. This provides great effects, e.g., omission of cumbersome operations after the use of the flowmeter, such as disinfection and sterilization.

What is claimed is:

1. A respiratory air flowmeter comprising: a flow path forming member for forming a flow path in which respiratory air flows, said member having a restricting segment interposed between a first segment and a second segment, each having an inner diameter larger than said restricting segment, said restricting segment including a third segment interposed between a contracting segment coupled to said first segment and the third segment, and an expanding segment coupled to said third segment and said second segment, wherein said restricting segment of said flow path forming member stabilizes the respiratory air flow;
   a rectifying means within said first and second segments of the flow path, arranged with spacing between said means, and disposed symmetrically to the center of the flow path, for stabilizing a respiratory air flow; and
   a microsensor having a silicon body and a flow detecting means, said flow detecting means being thermally insulated from the microsensor by an etched pit beneath said flow detecting means, disposed in said restricting segment of said flow path, said microsensor mounted on an inner wall of said flow path forming member, for detecting a flow rate of respiratory air flowing in the flow path.

2. A flowmeter according to claim 1, further comprising
   a sensor mounting portion having a sensor window and formed in the restricting portion of said flow path forming member, said sensor mounting portion having a seat surface on which said sensor is mounted,
   a gasket arranged on said sensor mounted on the seat surface,
   a lid arranged on said gasket, and
   a fixing member for fixing said gasket and said lid on said sensor mounting portion and sealing said mounted gasket and lid.

3. A flowmeter according to claim 1, further comprising
   a sensor mounting portion having a sensor window and formed in the restricting portion of said flow path forming member, said sensor mounting portion having a seat surface on which said sensor is mounted, and
   an adhesive tape for fixing said sensor on the seat surface and sealing said mounted sensor.

4. A respiratory air flowmeter according to claim 1 wherein said rectifying means includes a rectifying lattice.

5. A respiratory air flowmeter according to claim 1 wherein said rectifying means includes a rectifying screen.

6. A respiratory air flowmeter according to claim 4 wherein said flow detecting means includes a flow detecting diaphragm.

7. A respiratory air flowmeter according to claim 5 wherein said flow detecting means includes a flow detecting diaphragm.

8. A respiratory air flowmeter according to claim 4 wherein said flow detecting means includes a flow detecting bridge.

9. A respiratory air flowmeter according to claim 5 wherein said flow detecting means includes a flow detecting bridge.

* * * * *